(12) United States Patent
Hansmann et al.

(10) Patent No.: US 9,885,730 B2
(45) Date of Patent: Feb. 6, 2018

(54) MAGAZINE DEVICE, MEASURING SYSTEM AND METHOD FOR MEASURING A CONCENTRATION OF GASEOUS AND/OR AEROSOL COMPONENTS OF A GAS MIXTURE

(71) Applicant: Dräger Safety AG & Co. KGaA, Lübeck (DE)

(72) Inventors: Hans-Ullrich Hansmann, Barnitz (DE); Philipp Rostalski, Lübeck (DE); Jan Boeckmann, Lübeck (DE)

(73) Assignee: Dräger Safety AG & Co. KGaA, Lübeck (DE)

( * ) Notice: Subject to any disclaimer, the term of this patent is extended or adjusted under 35 U.S.C. 154(b) by 0 days.

(21) Appl. No.: 14/926,532

(22) Filed: Oct. 29, 2015

(65) Prior Publication Data

US 2016/0124004 A1 May 5, 2016

(30) Foreign Application Priority Data

Oct. 30, 2014 (DE) .......................... 10 2014 015 945

(51) Int. Cl.
*B01L 3/00* (2006.01)
*A61J 1/06* (2006.01)
*G01N 21/00* (2006.01)
*G01N 35/00* (2006.01)
*G01N 21/75* (2006.01)
(Continued)

(52) U.S. Cl.
CPC ....... *G01N 35/00029* (2013.01); *G01N 21/75* (2013.01); *G01N 31/223* (2013.01); *G01N 33/0013* (2013.01); *G01N 35/04* (2013.01); *G01N 2035/00089* (2013.01);
(Continued)

(58) Field of Classification Search
CPC ............... A61J 1/06; G01N 21/00; B01L 3/00
USPC ...... 422/63, 64, 65, 66, 68.1, 547, 551, 552, 422/553, 554, 560, 561; 436/43
See application file for complete search history.

(56) References Cited

U.S. PATENT DOCUMENTS 3,526,480 A * 9/1970 Reid ........................ B01L 3/545
356/38
5,501,984 A * 3/1996 Hofstetter .......... G01N 35/1065
422/63
(Continued)

FOREIGN PATENT DOCUMENTS

DE              10 93 113 B      11/1960
DE        10 2013 006 542 A1    10/2014
DE        10 2013 006 548 A1    10/2014

*Primary Examiner* — Brian J Sines
(74) *Attorney, Agent, or Firm* — McGlew and Tuttle, P.C.

(57) ABSTRACT

A magazine device (14) and method are provided for a measuring device (12) for measuring a concentration of gaseous and/or aerosol components of a gas mixture. The magazine device (14) includes a holding device (16) for a plurality of reaction carriers (18), which have each at least one reaction chamber with a reactant. The reactant is designed to react with a particular component to be measured in the gas mixture or with a reaction product of the component to be measured in an optically detectable manner. A feed device (20) removes a reaction carrier (18) of the plurality of reaction carriers (18) from the holding device (16) and feed the reaction carrier to the measuring device (12) for carrying out a measurement of the particular component to be measured in the gas mixture. A control unit (22) controls the holding device (16) and/or the feed device (20).

7 Claims, 3 Drawing Sheets

(51) Int. Cl.
*G01N 31/22* (2006.01)
*G01N 33/00* (2006.01)
*G01N 35/04* (2006.01)

(52) U.S. Cl.
CPC .................. *G01N 2035/042* (2013.01); *G01N 2035/0465* (2013.01); *G01N 2035/0489* (2013.01)

(56) References Cited

U.S. PATENT DOCUMENTS

| | | | | |
|---|---|---|---|---|
| 6,167,767 | B1* | 1/2001 | Mengel | G01N 1/2273 73/863.01 |
| 6,357,984 | B1* | 3/2002 | Zinger | H01L 21/67766 414/331.05 |
| 2004/0120861 | A1* | 6/2004 | Petroff | B01L 3/502715 422/400 |
| 2010/0158643 | A1* | 6/2010 | Friedman | H01L 21/67715 414/222.01 |

\* cited by examiner

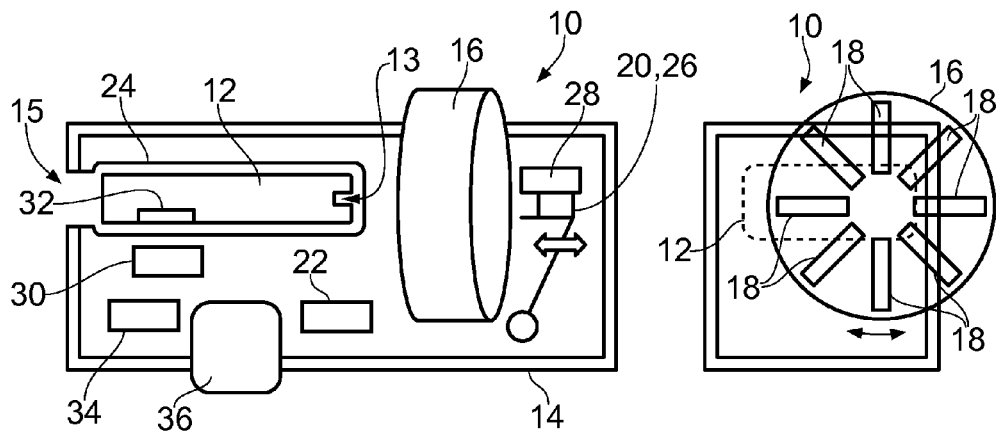
FIG. 1
FIG. 2
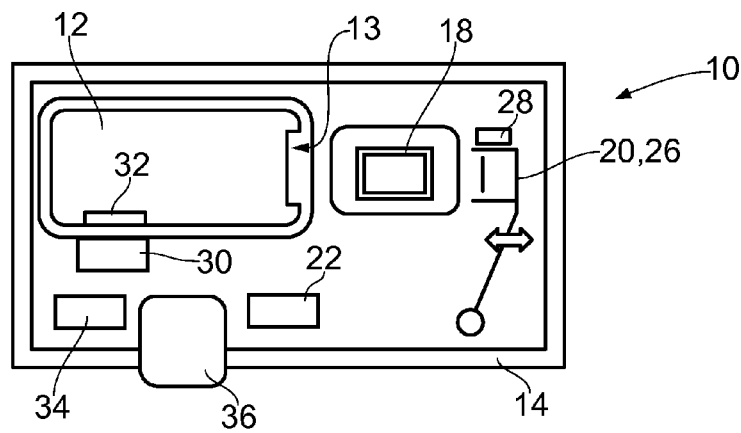
FIG. 3
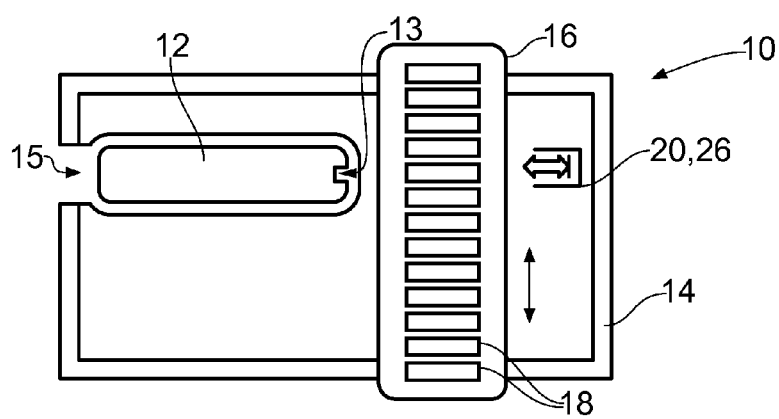
FIG. 4

MAGAZINE DEVICE, MEASURING SYSTEM AND METHOD FOR MEASURING A CONCENTRATION OF GASEOUS AND/OR AEROSOL COMPONENTS OF A GAS MIXTURE

CROSS REFERENCE TO RELATED APPLICATIONS

This application claims the benefit of priority under 35 U.S.C. § 119 of German Patent Application DE 10 2014 015 945.0 filed Oct. 30, 2014, the entire contents of which are incorporated herein by reference.

FIELD OF THE INVENTION

The present invention pertains to a measuring system and to a method for measuring a concentration of gaseous and/or aerosol components of a gas mixture as well as to a magazine device for such a measuring system.

BACKGROUND OF THE INVENTION

Gas detector tubes, which are filled with a reactant, which reacts with a certain chemical compound in an optically detectable manner, are known from the state of the art. For example, a defined quantity of a gas mixture is pumped here through the gas detector tube, for example, with a manual pump. A concentration of the chemical compound to be measured is subsequently determined by means of a discoloration of the reactant.

Moreover, so-called chip-based measuring systems are known, in which the reactant is provided in a plurality of reaction chambers, which are arranged on a reaction carrier and which can be used for one measurement each. The reaction carrier may be inserted into a measuring device, which detects the reaction carrier and performs a corresponding measuring method for measuring a concentration of the corresponding component of the gas mixture.

However, it is not possible in conventional measuring systems to perform multiple automated measurements. Furthermore, different reaction carriers with respective different reactants are required for measuring different components.

SUMMARY OF THE INVENTION

An object of the present invention is to provide an improved measuring system and an improved measuring method, which makes multiple and flexible automatic measurements possible.

This object of the present invention is accomplished by a magazine device for a measuring device for measuring a concentration of gaseous and/or aerosol components of a gas mixture which comprises a holding device for a plurality of reaction carriers, which have each at least one reaction chamber with a reactant. The reactant is designed to react with a particular component to be measured in the gas mixture or with a reaction product of the component to be measured in an optically detectable manner. The magazine device comprises, furthermore, a feed device, which is designed (configured) to remove a reaction carrier of the plurality of reaction carriers from the holding device and to feed it to the measuring device for performing a measurement of the particular component to be measured in the gas mixture, and a control unit for controlling the holding device and/or the feed device. A plurality of very similar or different measurements can be made in this way automatically in a series by means of very similar reaction carrier or reaction carriers with different reactants. A measuring device equipped with such a magazine device can thus perform a plurality of measurements independently. On the one hand, a simple and cost-effective, quasi-continuous measurement of consecutive random measurements is thus made possible. On the other hand, it is not necessary, due to the automation, for a user of the measuring device to enter a possible hazardous zone with the magazine device for each measurement and to need corresponding protective clothing. Furthermore, the operation of the measuring device can be simplified in case of complex measurements of a plurality of components to be measured, which require a plurality of different reaction carriers.

For example, the holding device makes it possible to accommodate at least five reaction carriers, preferably 36 reaction carriers or more.

According to one embodiment variant, the holding device is designed (configured) as a mobile device and has a motor in order to position a certain reaction carrier in a predetermined position. A simple design of the holding device, on the one hand, and of the feed device, on the other hand, is made possible in this way.

For example, the holding device may be designed (configured) as a rotatable carousel, in the form of a linearly movable bar or in the form of a chain designed as an endless chain.

Furthermore, the holding device is preferably designed (configured) as a removable device, especially in order to be able to be equipped with reaction carriers independently from the site of the magazine device and of the measuring device.

It is also possible, as an alternative, that the holding device is arranged immovably in the magazine device and the feed device is provided for transporting the selected reaction carriers into the predetermined position. No drive needs to be provided for the holding device in this way, but the feed device does, in general, require a complex drive.

Furthermore, a removing device may be provided, which is designed (configured) to remove a reaction carrier from the measuring device after a measurement has been performed and to feed it to the holding device or to a container for used reaction carriers. A reaction carrier can be removed in this way from the measuring device and returned into the holding device, as a result of which further measurements can be carried out with this reaction carrier later, especially after measurements have been performed with other reaction carriers.

It is possible, as an alternative, that a container for used reaction carriers is designed (configured) such that used reaction carriers are removed from the measuring device directly into the container after all possible measurements have been performed with the reaction carrier.

A detection device, which is designed (configured) to read information being stored on the reaction carriers, is preferably provided. For example, the component of the gas mixture that is to be measured with the reaction carrier, i.e., the type of the reactant, the number of measurements already performed or the number of still remaining measurements, i.e., the number of used or yet unused reaction chambers, or other information can be read in this way. This makes possible, for example, an independent selection of a suitable reaction carrier by the magazine device or ensures the correct selection of a reaction carrier. The detection device can communicate with the reaction carrier, for example, by near-field communication, read optical information, for example, a bar code, on the reaction carrier, or read information stored on the reaction carrier in another manner.

The control unit may be designed (configured) to control a feed of the reaction carriers arranged in the holding device to the measuring device in a predetermined order. This makes possible a simple control of the magazine device, which is suitable, for example, for a long measurement series of very similar measurements, in which very similar reaction carriers are used.

According to a preferred embodiment, a communication device is provided that is configured for communication with the measuring device. Information can be exchanged in this way between the measuring device and the magazine device.

The control unit may be designed (configured), in particular, to control a feed of the reaction carriers arranged in the holding device to the measuring device as a function of a result of a preceding measurement. A series of consecutive measurements can be adapted in this way to the measurement results. For example, a time interval between consecutive measurements can be shortened in case a component to be measured is detected in the gas mixture, or measurements of certain other components may be performed by means of different reactants/reaction carriers in response to the detection of a certain component in the gas mixture.

The control unit may be preferably programmed by a user, so that the type of the consecutive measurements, the time interval between the measurements and the dependence of the measuring method on the measurement results can be set by the user. It is possible, as an alternative, that the control unit be provided as a control unit of the measuring device or as an external control unit, which communicates with the magazine device and/or the measuring device, and can be programmed instead of providing the control unit at or associated only with the magazine device.

The present invention pertains, furthermore, to a measuring system, for measuring a concentration of gaseous and/or aerosol components of a gas mixture, with an above-described magazine device and with a measuring device, wherein the measuring device has a measuring unit for drawing in the gas mixture through a reaction chamber of the reaction carrier fed to the measuring device, for detecting the optically detectable reaction, and for determining the concentration of the component to be measured in the gas mixture.

The measuring device is preferably designed (configured) as an independent device, and the magazine device has a holder, in which the measuring device is removably accommodated. The measuring device can be used flexibly in this way, on the one hand, for automatic measurement series, and, on the other hand, in the mobile form for manual measurements. The measuring device may have a compact, lightweight and handy design in this way and thus it facilitates manual measurements without the magazine device, which may be relatively large and heavy, especially in a large holding device.

The mentioned object of the present invention is accomplished, furthermore, by a method for measuring a concentration of gaseous and/or aerosol components of a gas mixture with a measuring system, which comprises a measuring device, a holding device for a plurality of reaction carriers and a feed device. The method comprises the method steps of selecting a first reaction carrier from among a plurality of reaction carriers in the holding device, wherein the first reaction carrier has at least one reaction chamber with a first reactant and the first reactant is designed to react with a first component to be measured in the gas mixture or with a reaction product of the first component to be measured in an optically detectable manner; of removing the first reaction carrier from the holding device and feeding the first reaction carrier to the measuring device by the feed device; and of performing at least one first measurement of the first component to be measured in the gas mixture by the measuring device. The method comprises, furthermore, the method steps of selecting a second reaction carrier from among the plurality of reaction carriers in the holding device, wherein the second reaction carrier has at least one reaction chamber with a second reactant and the second reactant is designed to react with a second component to be measured in the gas mixture or with a reaction product of the second component to be measured in an optically detectable manner; of removing the second reaction carrier from the holding device and feeding the second reaction carrier to the measuring device by the feed device; and of performing at least one second measurement of the second component to be measured in the gas mixture by the measuring device. Consecutive measurements can be carried out in this way automatically with a plurality of reaction carriers.

According to one method variant, a measurement of the same component to be measured in the gas mixture is performed repeatedly in a predetermined time interval. This makes it possible to automatically perform a long measurement series. In particular, the first and second reaction carriers may have the same reactant.

According to another method variant, consecutive measurements of different components of the gas mixture are performed, and the first and second reaction carriers have different reactants. This makes it possible to automatically perform complex measurements, in which a plurality of components to be measured in a gas mixture shall be measured.

According to a preferred method variant, a time interval is selected between consecutive measurements and/or the reaction carrier is selected from among a plurality of reaction carriers with different reactants as a function of a measurement result of the first measurement. The measuring method can be automatically adapted in this way as a function of the measurement results.

To make possible a broadest possible measurable concentration range with automatic measurements, at least two reaction carriers are preferably provided in the holding device, which reaction carriers are designed each for the detection of the same gaseous and/or aerosol component to be measured, and the reactants of the two reaction carriers contained therein differ in that they are designed for the measurement of the component to be measured in respective different concentration ranges. A selection of the reaction carrier from among the at least two reaction carriers with different concentration ranges is made as a function of a measurement result of the first measurement.

Further advantages and features of the present invention appear from the following description and from the figures, to which reference is made. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

BRIEF DESCRIPTION OF THE DRAWINGS

In the drawings:

FIG. 1 is a top view of a measuring system according to the present invention with a magazine device according to the present invention;

FIG. 2 is a side view of the measuring system and of the magazine device from FIG. 1;

FIG. 3 is a top view of a measuring system with a magazine device according to a second embodiment of the present invention;

FIG. 4 is a side view of the measuring system and of the magazine device from FIG. 3;

DESCRIPTION OF THE PREFERRED EMBODIMENTS

Figures 5, 6:
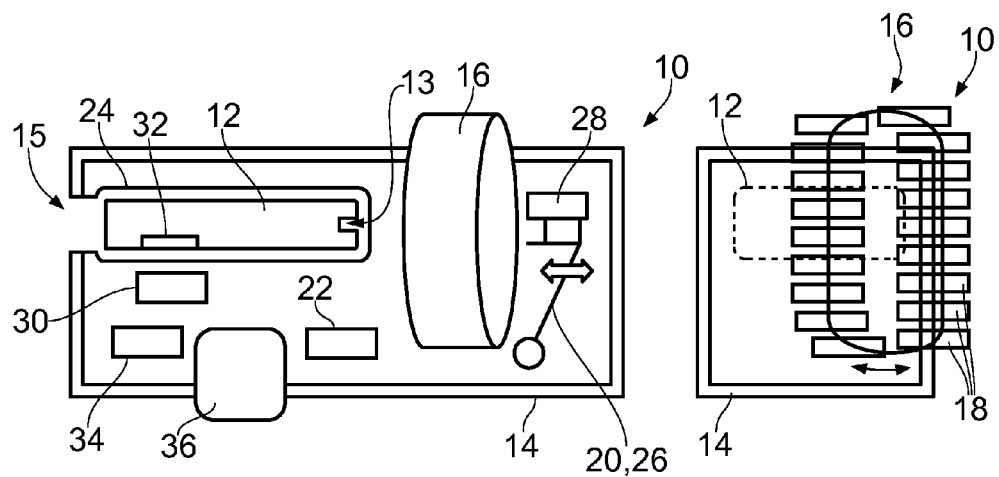
FIG. 5 is a top view of a measuring system with a magazine device according to a second embodiment of the present invention.
FIG. 6 is a side view of the measuring system and of the magazine device from FIG. 5.

Referring to the drawings, FIG. 1 and FIG. 2 show a measuring system 10 with a measuring device 12 for measuring a concentration of gaseous and/or aerosol components of a gas mixture and with a magazine device 14. The measuring device 12 can be inserted into and removed from the magazine device 14 through an opening 15 of the magazine device 14 in the embodiment being shown. Operation of the measuring device 12 with and without the magazine device 14 is possible in this way. However, it is also possible, in principle, that the measuring device 12 and the magazine device 14 are integrated in a common integral device.

The measuring device 12 comprises a measuring unit, which draws in the gas mixture and sends it through a reaction chamber, in which a reactant is provided, which is designed to react with a particular component to be measured in the gas mixture or with a reaction product of the component to be measured in an optically detectable manner. The optically detectable reaction is detected by an optical sensor of the measuring unit and analyzed for determining the concentration of the component to be measured in the gas mixture. The reaction chamber is formed on a replaceable reaction carrier 18, and, in particular, a plurality of different types of reaction carriers 18 may be provided, which are provided each with different reactants in order to make possible in this way a measurement of a plurality of different components.

A plurality of reaction chambers, which make it possible to perform different measurements independently, in which a reaction chamber each is used, are advantageously arranged on a reaction carrier 18. It is possible that very similar reaction chambers with the same reactant are arranged on one reaction carrier 18. However, it is also possible that different reaction chambers with reactants that are designed each for different components to be measured or for different concentration ranges of the same component to be measured are arranged on a reaction carrier 18.

The measuring system 10 makes it possible to carry out automatically a plurality of very similar or different measurements, which require a plurality of reaction carriers 18. Therefore, no user needs to be present at the location of the measuring system 10 during the operation of the measuring system 10. This is especially advantageous in case of poorly accessible locations and in locations that can only be entered while wearing protective clothing.

In the embodiment being shown, the measuring device 12 has an insertion opening 13 for the reaction carriers 18, via which the reaction carriers 18 can be inserted for carrying out a corresponding measurement. After at least one measurement has been performed with the inserted reaction carrier 18, the reaction carrier is ejected again via the insertion opening 13. It is also possible, as an alternative, to provide a separate removal opening on the measuring device 12, for example, at the end of the measuring device 12 located opposite the insertion opening 13, through which the reaction carrier is ejected.

The magazine device 14 comprises a holding device 16 for a plurality of reaction carriers 18, which have at least one reaction chamber each with a reactant. The reaction carriers 18 preferably have a plurality of reaction chambers each, for example 10 or more, and thus make it possible to carry out independently a plurality of different measurements at different times.

The magazine device 14 comprises, furthermore, a feed device 20, which is designed (configured) to remove a reaction carrier 18 of the plurality of reaction carriers 18 from the holding device 16 and to feed this reaction carrier 18 to the measuring device 12 for carrying out a measurement of the particular component to be measured in the gas mixture.

A control unit 22 is provided for controlling the holding device 16 and the feed device 20.

The magazine device 14 makes it possible to carry out a plurality of very similar or different measurements automatically, by means of very similar reaction carriers or reaction carriers containing different reactants. The measuring device 12 can thus carry out quasi-continuous measurements by consecutive random measurements in a simple and cost-effective manner.

It is not necessary due to the automation for a user of the measuring device 12 to enter a possibly hazardous zone with the magazine device 14 for each measurement wearing corresponding protective clothing.

Furthermore, the operation of the measuring device 12 is simplified in case of complex measurements of a plurality of components to be measured, which requires a plurality of different reaction carriers 16, due to the fact that a sequence of different measurements can be programmed and an automatic changeover of different reaction carriers 18 in the holding device 16 is made possible by the control unit 22.

In the first embodiment in FIGS. 1 and 2, the holding device is designed (configured) as a rotatable carousel, which can accommodate eight reaction carriers 18.

The measuring device 12 is designed (configured) as an independent device in the embodiment being shown, and the magazine device 14 has a holder 24, in which the measuring device 12 is removably accommodated.

The measuring device 12 can thus be inserted in a flexible manner; on the one hand, the measuring device 12 can be inserted into the magazine device 14 for automatic measurement series, and, on the other hand, it can be removed from the magazine device 14 for mobile, manual measurements. The measuring device 12 has a compact, lightweight and handy design and thus makes possible simple manual measurements without the magazine device 14, which may be relatively large and heavy especially in case of a large holding device 16.

The holding device 16 has a motor, which rotates the carousel in order to position a certain reaction carrier 18 in a predetermined position, which is located opposite an insertion opening 13 for reaction carriers 18 of the measuring device 12 when the measuring device 12 is received in the holder 24.

The holding device 16 is designed (configured) as a removable device, as a result of which the holding device 16 can be equipped with reaction carriers 18 independently from the location of the magazine device 14 and of the measuring device 12. The holding device 16 is preferably replaceable, so that rapid replacement of a holding device 16 present in the magazine device 14 with a newly equipped holding device 16 is made possible.

It is also possible, as an alternative, that a holding device 16 is arranged immovably in the magazine device 14 and the feed device is designed (configured) for transporting the selected reaction carrier 18 such that it grasps the selected reaction carrier 18 in a first position in the holding device and transports it into a second, predetermined position at the measuring device 12 and feeds it to the measuring device in the second position, wherein especially a multiaxial motion of the feed device may be provided.

Moreover, the feed device 20 also forms in the embodiment being shown a removing device, which is designed (configured) to remove the selected reaction carrier 18 from the measuring device 12 after a measurement has been performed and to feed it to the holding device 16 or to a container for used reaction carriers 18. The reaction carrier 18 is removed in this way from the measuring device 12 and returned into the holding device 16, as a result of which further measurements can be carried out with this reaction carrier 18 later, especially after measurements have been performed with other reaction carriers 18.

It is possible, as an alternative, that a container for used reaction carriers 18 is designed (configured) such that used reaction carriers 18 are removed from the measuring device 12 directly into the container after all possible measurements have been performed with the reaction carrier 18.

A detection device 28, which is designed (configured) to read information being stored on the reaction carriers 18, is provided on the feed device 20. The component that is to be measured in the gas mixture with the reaction carrier, i.e., the type of the reactant, the number of measurements already performed or the number of measurements yet to be performed, i.e., the number of used or yet unused reaction chambers, are read in the preferred embodiment. The magazine device 14 can thus reliably perform an independent selection of a suitable reaction carrier 18 for carrying out a certain measurement or a checking whether a reaction carrier 18 was selected correctly. The detection device 28 can communicate with the reaction carrier 18 by near-field communication in the embodiment being shown.

As an alternative, the detection device 28 may be designed (configured), for example, as an optical sensor in order to read optical information, for example, a bar code, on the reaction carrier or to read other information being stored on the reaction carrier in another manner.

The information may also be stored when inserting the holding device 16 in the control unit 22 and updated at the time of each measurement.

In the preferred embodiment, the control unit 22 may be operated in different modes.

In a first mode, the control unit is configured to feed the reaction carriers arranged in the holding device to the measuring device in a predetermined sequence. This makes possible a simple control of the magazine device, which is suitable, for example, for a long measurement series of very similar measurements, in which very similar reaction carriers are used. No communication is necessary between the measuring device 12 and the magazine device 14 for automation in this case. The magazine device 14 or the measuring device 12 or the measuring system 10 must only be able to detect when a replacement of the reaction carrier 18 has to be performed. This may be made possible, for example, by a mechanical or optical sensor, which can detect a certain position of a reaction carrier 18 located in the measuring device 12 and detects, for example, an ejection position of a used reaction carrier 18 ejected from the measuring device 12 or the absence of a reaction carrier 18 in the measuring device 12.

To make communication with the measuring device 12 possible for more complex modes of operation, a communication device 30 is provided for communication with the measuring device 12. Information can be exchanged in this way between the measuring device 12 and the magazine device 14. A wireless near-field communication device 30, which communicates with a corresponding near-field communication device 32 of the measuring device 12, is provided in the embodiment being shown. However, other communication devices may be provided as well. In particular, the measuring device 12 may also be connected to the magazine device 14 via an interface or a cable.

In a second mode of operation, the control unit 22 is configured to feed the reaction carriers 18 arranged in the holding device 16 to the measuring device 12 as a function of a result of a preceding measurement. A series of consecutive measurements are adapted in this way to the measurement results. For example, if a certain component to be measured is detected in the gas mixture, a time interval between consecutive measurements is shortened or a measurement of a certain second other component is performed by means of a different reactant/reaction carrier in response to the detection of a first component in the gas mixture.

The control unit 22 may be programmed by a user, so that the nature of the consecutive measurements, the time interval between the measurements and the dependence of the measuring method on the measurement results can be set by the user. It is possible, as an alternative, that a control unit of the measuring device 12 or an external control unit, which communicates with the magazine device 14 and/or with the measuring device 12, is programmed instead of the control unit 22 of the magazine device 14, and it sends corresponding commands to the control unit 22 of the magazine device 14.

Furthermore, the magazine device 14 comprises an independent energy supply 34 in the form of a battery, which guarantees especially the function of the magazine device 14 even in case of outage of a possible external energy supply. The energy supply 34 may also be designed (configured) to be able to supply the measuring device 12 with energy, whereby, for example, a longer operation of the measuring device 12 and thus of the entire measuring system 10 is made possible.

The embodiment being shown comprises, moreover, an external communication unit 36, which makes communication possible with the user and/or external devices. In a simple embodiment, the external communication unit 36 is a local alarm, which sends an acoustic and/or optical warning signal when the measuring device 12 measures a certain concentration of a certain component in the gas mixture. The user can also be warned in this way in case of automatic operation of the measuring device 12. However, the external communication unit 36 is designed (configured) as a wireless communication design in the preferred embodiment, which makes possible a wireless communication with external devices. The measuring system 10 can be integrated in this way into an external alarm chain and the measurement results and/or a corresponding warning can be transmitted to a central control station, which can trigger a general alarm and/or emergency call.

FIGS. 3 and 4 show a second embodiment of the magazine device 14, which differs from the magazine device 14 according to the first embodiment by the mode of construction of the holding device. In the second embodiment, the holding device 16 is designed (configured) in the form of a linearly movable bar. The holding device 16 has a motor, which can linearly move the holding device 16 tangentially to the measuring device 12 in order to position a certain reaction carrier 18 in a predetermined position in relation to the insertion opening 13 of the measuring device 12. In this predetermined position, the feed/removing device 20, 26 can grasp the certain reaction carrier 18 and insert the particular reaction carrier 18 into the insertion opening 13 of the measuring device 12. The holding device 16 thus has a simple mode of construction and can accommodate many reaction carriers 18 in a narrow space.

FIGS. 5 and 6 show a third embodiment of the magazine device 14, which differs from the magazine device 14 according to the first embodiment by a holding device 16 in the form of an endless chain. A plurality of holders for reaction carriers 18 are flexibly connected to one another and form a closed chain. A motor and a deflecting mechanism are provided, which make possible the circulation of the chain, so that a certain reaction carrier 18 can be positioned in one of the holders in a predetermined position in relation to the insertion opening 13 of the measuring device 12. The feed/removing device 20, 26 can grasp the particular reaction carrier 18 in this predetermined position and insert the certain reaction carrier 18 into the insertion opening 13 of the measuring device 12. A small space is needed for installing the entire arrangement of the magazine device 14 in this mode of construction.

Figure 7:
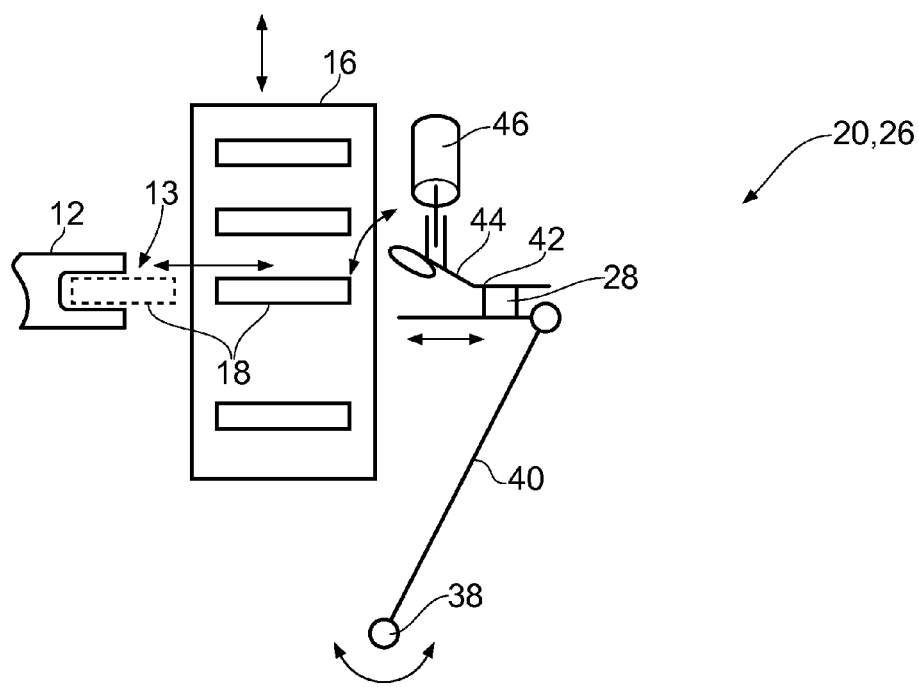
FIG. 7 is a schematic view of a first embodiment of a feed device of a magazine device according to the present invention.

FIG. 7 shows a first embodiment variant of the feed/removing device 20, 26. A first motor 38 is provided to rotate a lever 40. A gripper 42 for a reaction carrier 18 is arranged at the other end of the lever 40. The gripper 42 comprises a movable gripping finger 44, which is moved by a second motor 46 in order to grasp a reaction carrier 18.

The feed/removing device 20, 26 is shown in a starting position in FIG. 7. The gripper 42 is arranged at a spaced location from the holding device 16 in the starting position, so that a motion of the holding device 16 is made possible for positioning a certain reaction carrier 18 in relation to the insertion opening 13 of the measuring device 12. After positioning the reaction carrier, the gripper 42 moves, driven by the first motor 38, towards the reaction carrier 18, and the gripping finger 44 is closed by the second motor, so that the reaction carrier 18 is clamped by the gripping finger 44 in the gripper 42.

The gripper 42 with the reaction carrier 18 is subsequently moved by the first motor 38 in the direction of the measuring device 12, so that the reaction carrier 18 is inserted into the insertion opening 13 of the measuring device 12.

The removal of the reaction carrier 18 after the measurement takes place analogously in the reverse sequence.

Figure 8:
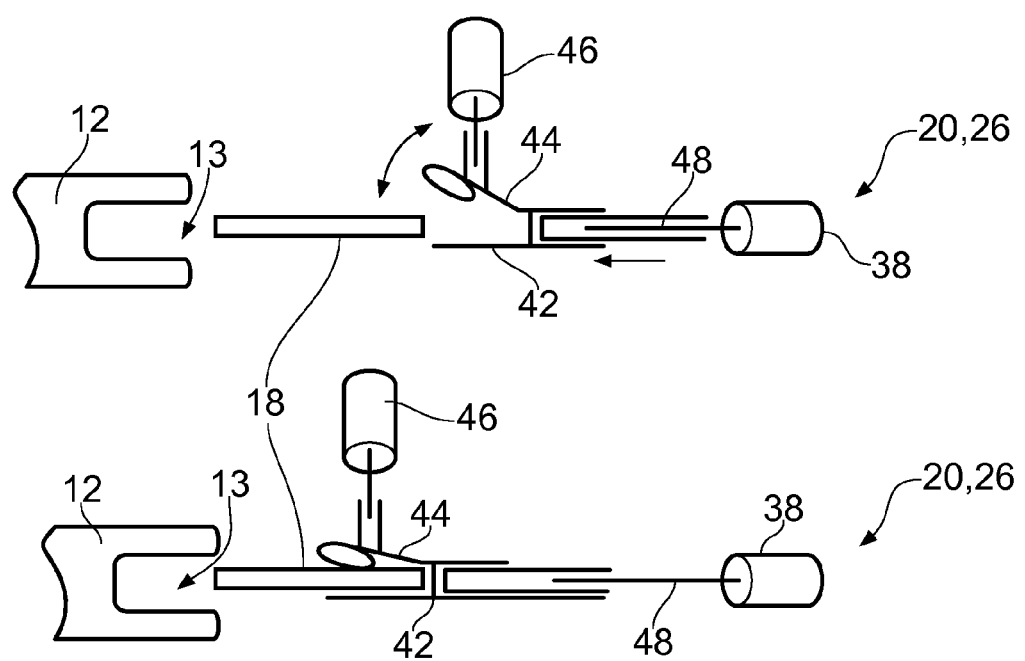
FIG. 8 is a schematic view of a second embodiment of a feed device of a magazine device according to the present invention.

FIG. 8 shows a second embodiment of the feed/removing device 20, 26. The gripper 42 is designed (configured) analogously to the preceding embodiment. The first motor 38 is formed by a line drive with a threaded rod 48 here. The feed/removing device 20, 26 is shown in the upper half of the figure in its starting position analogously to the preceding embodiment variant. The feed/removing device 20, 26 is shown in the lower half of the figure in the position in which it grasps the reaction carrier 18. The feed/removal operation is carried out analogously to the above-described embodiment variant shown in FIG. 7.

A method for measuring a concentration of gaseous and/or aerosol components of a gas mixture with a measuring system 10 will be described below on the basis of FIGS. 1 and 2.

In a first step, a first reaction carrier 18 is selected from among a plurality of reaction carriers 18 in the holding device 16, the first reaction carrier having at least one reaction chamber with a first reactant and the first reactant being designed to react with a first component to be measured in the gas mixture or with a reaction product of the first component to be measured in an optically detectable manner. This happens, for example, based on a defined position of the reaction carrier 18 in the holding device and/or based on information stored on the reaction carrier 18, which is read by the detection device 28.

The first reaction carrier 18 is subsequently removed by the feed device 20, as was described above, from the holding device 16 and fed to the measuring device.

A first measurement of a first component to be measured in the gas mixture is performed by means of the first reaction carrier 18.

The first reaction carrier 18 is removed from the measuring device 12 after the first measurement by the removing device 26, as was described above, and returned to its preceding position in the holding device 16. In case all reaction chambers of the reaction carrier 18 have been used and the reaction carrier has thus been used up, it is also possible that the reaction carrier is transported into a container for used reaction carriers.

The measuring device 12 is subsequently ready for a further measurement. Analogously to the first reaction carrier 18, a second reaction carrier 18 is selected in the further method steps from among the plurality of reaction carriers 18 in the holding device 16, the second reaction carrier 18 having at least one reaction chamber with a second reactant and the second reactant being designed to react with a second component to be measured in the gas mixture or with a reaction product of the second component to be measured in an optically detectable manner. The second reaction carrier 18 is correspondingly removed from the holding device 16 and the second reaction carrier 18 is fed to the measuring device 12 by the feed device 20, and at least one second measurement of the second component to be measured in the gas mixture is carried out by the measuring device 12.

In one mode of operation, a measurement of the same component to be measured in the gas mixture is performed repeatedly at a predetermined time interval, as a result of which a long measurement series with a plurality of measurements is automatically performed. To make the longest possible measurement series possible, for example, all reaction carriers 18 in the holding device are of the same type, i.e., they have the same reactant. The reaction carrier does not have to be replaced after each measurement in this case, but it may remain in the measuring device until all reaction chambers of the reaction carrier have been used.

However, it is also possible that different measurements are carried out alternatingly with different reaction carriers 18, and consecutive measurements of different components of the gas mixture are performed, the first and second reaction carriers 18 containing different reactants. This makes it possible to automatically perform more complex measurements, in which a plurality of components to be measured in a gas mixture shall be measured.

Communication is provided in the embodiments being shown between the measuring device 12 and the magazine device 14. This enables the user to program complex automatic measurements as a function of preceding measurement results. For example, a time interval is selected between consecutive measurements and/or the reaction carrier is selected from among a plurality of reaction carriers having different reactants as a function of a measurement result of the first measurement.

For example, the time interval can thus be shortened in case of a rising concentration of a component in order to obtain a better time resolution of the measurement series in order to detect a further rise in a timely manner. Flexible follow-up measurements of other components can be made in case certain components are detected. Other measured data may also be detected, for example, a temperature by means of a temperature sensor, in which case a measurement of a certain component of the gas mixture is triggered by actual values above or below temperature limits or gradients.

Furthermore, it is also possible to provide two reaction carriers 18, which have different sensitivity ranges for a certain component and are thus designed for measuring the component to be measured in different concentration ranges, the reaction carrier 18 being selected from among the at least two reaction carriers 18 with different concentration ranges as a function of a measurement result of the first measurement. For example, a further follow-up measurement is performed with a reaction carrier 18 with a lower saturation in case of a measurement in which a reaction carrier 18 with high sensitivity was saturated. It is also possible that the reaction carrier 18 is selected from among the at least two reaction carriers 18 with different concentration ranges as function of a measurement result for another component to be measured.

It is possible, as an alternative, that a follow-up measurement is carried out with a very similar reaction chamber on the same reaction carrier 18 or with another, very similar reaction carrier 18, in which case the measuring device 12 makes possible a changed sensitivity of the measurement due to a change in the measurement parameters, for example, the volume flow of the gas mixture.

A measuring process may be programmed via the magazine device 14, the measuring system 10 or an external control unit.

While specific embodiments of the invention have been shown and described in detail to illustrate the application of the principles of the invention, it will be understood that the invention may be embodied otherwise without departing from such principles.

APPENDIX

List of Reference Numbers

10 Measuring system
12 Measuring device
13 Insertion opening
14 Magazine device
15 Opening
16 Holding device
18 Reaction carrier
20 Feed device
22 Control unit
24 Holder
26 Removing device
28 Detection device
30 Communication device
32 Communication device
34 Energy supply
36 Communication unit
38 Motor
40 Lever
42 Gripper
44 Gripping finger
46 Motor
48 Threaded rod

What is claimed is:

1. A magazine device for a measuring device for measuring a concentration of gaseous and/or aerosol components of a gas mixture, the magazine device comprising:
    a holding device configured to hold a plurality of reaction carriers, the reaction carriers each having at least one reaction chamber with a reactant, the reactant being designed to react with a particular component to be measured in the gas mixture or with a reaction product of the component to be measured in an optically detectable manner;
    a feed device configured to remove one of the reaction carriers from among the plurality of reaction carriers from the holding device and to feed the one of the reaction carriers to the measuring device for carrying out a measurement of the particular component to be measured in the gas mixture, wherein a concentration of gaseous and/or aerosol components of the gas mixture is measured via the measuring device when the one of the reaction carriers is at the measuring device; and
    a control unit controlling at least one of the holding device and the feed device.

2. A magazine device in accordance with claim 1, wherein the holding device is configured as a mobile device and further comprising a motor to position a certain reaction carrier in a predetermined position.

3. A magazine device in accordance with claim 1, further comprising a removing device configured to remove the one of the reaction carriers from the measuring device after a measurement has been performed and to feed the removed reaction carrier to the holding device or to a container for used reaction carriers.

4. A magazine device in accordance with claim 1, further comprising a detection device configured to read information stored on the reaction carriers.

5. A magazine device in accordance with claim 1, wherein the control unit is programmed to control a feed of the reaction carriers arranged in the holding device to the measuring device in a predetermined sequence.

6. A magazine device in accordance with claim 1, further comprising a communication device configured for communication with the measuring device.

7. A magazine device in accordance with claim 6, wherein the control unit is programmed to control a return of the reaction carriers arranged in the holding device to the measuring device as a function of a result of a preceding measurement.

* * * * *